(12) United States Patent
Israel

(10) Patent No.: US 6,245,381 B1
(45) Date of Patent: Jun. 12, 2001

(54) MANUFACTURE OF COMPOSITE ROOFING PRODUCTS WITH MATRIX FORMULATED MICROBIOCIDE

(76) Inventor: Michael G. Israel, 14895 Feather Cove Rd., Clearwater, FL (US) 33762

( * ) Notice: Subject to any disclaimer, the term of this patent is extended or adjusted under 35 U.S.C. 154(b) by 0 days.

(21) Appl. No.: 09/438,615

(22) Filed: Nov. 12, 1999

(51) Int. Cl.[7] .................................................. B05D 1/12
(52) U.S. Cl. ........................................... 427/186; 427/188
(58) Field of Search ..................................... 427/186–188, 427/407.1; 428/141, 142, 144, 148

(56) References Cited

U.S. PATENT DOCUMENTS 5,573,810 * 11/1996 Grubka .

5,599,586 * 2/1997 Israel .

* cited by examiner

Primary Examiner—Fred J. Parker

(57) ABSTRACT

This invention discloses improved residential roofing products with durable active protection against algae discoloration. Versatile organometallic salts and chelates for this purpose are incorporated in manufacture of composite concrete tile and asphalt shingle products via integrated process modifications. These chemically stable non-volatile microbiocides, with exceptional effectiveness against both green and blue green algae, are tailored for specific matrix compatibility. By virtue of their composition and surface activity they serve a dual function in process improvement and product performance. The control of microbiocide activity, long term, significantly advances the state-of-the-art protection against algae and the service life of these products.

15 Claims, No Drawings

MANUFACTURE OF COMPOSITE ROOFING PRODUCTS WITH MATRIX FORMULATED MICROBIOCIDE

BACKGROUND OF THE INVENTION

1. Field of Invention

This invention relates to versatile active microbiocides which provide durable protection for composite roofing products.

2. Description of the Prior Art

Technical advances in the manufacture of residential roofing are being compromised by increasing maintenance requirements and environmental threats posed by the products in the marketplace. These problems are associated with unsightly algae growth on both concrete tile and asphalt shingle roofs which dominate the market. Most severe in warm moist climates, algae proliferation due to storm turbulence, high density planned communities and manufacturing processes gives cause for alarm considering the inherent transient uncontrollable algae inhibitors on which the technology is established. Evidence of viable alternatives to achieve projected product life and avoid service requirements is lacking in these industry segments. The prevailing conventional wisdom would deny the most fundamental observations regarding the nutrient value of calcium carbonate in sustaining autotropic biological growth and the threshold lethal dosage of ionic divalent metal compounds. And the increasing incidence of warranted product failures and pro-rated remedies can only be reconciled by loss of manufacturer identity in the marketplace.

Historically, the concrete tile industry has represented the high end roofing product in terms of esthetics, prestige, structural requirements and cost. The system relies on the integral granular surfaced roll roof which the tile serve to protect for traditionally forty year roof life. Concrete tiles, produced from a range of processes and compositions, were the first to evidence unacceptable roof discoloration and actually spawned the now mature cleaning and painting service sector. While this industry has not actively pursued algae inhibition per se, efforts to reduce efflorescence through the use of sealants and coatings have provided some measure of relief. Cast tile products retain relatively high moisture to support algae growth and typically quality for maintenance cleaning service the year of installation. Extruded tile are more consolidated and are optionally sealed and surfaced coated. The application of internal sealant is intended to reduce moisture intrusion as the source of efflorescence and initial algae discoloration is slower to develop. Improvements achieved with supplemental glaze coatings can extend maintenance free life to approximately 7 years. Ultimate loss of the surface coatings by weathering qualifies the roof for routine cleaning maintenance with accompanying reduction in product life. Mechanical fastening versus masonry or foam adhesives used to secure tiles also effect moisture retention and algae growth in these systems. Growing attention to algae discoloration in southern markets has prompted an increased use of heat absorbing dark colors and replacement of tile with the shorter life asphalt shingle roof. In addition, home owner associations increasingly enforce maintenance standards with little or no substantive information on the damage incurred by the service.

In contrast the asphalt shingle industry records early concern for the algae discoloration with studies on characterization and algae resistance (AR) technology. The composite roll product also used in the tile roofing system is produced on high speed web lines in which a base mat is saturated with molten asphalt and surfaced with ceramic coated granules which are embedded by roll pressing. This product is optionally cut on line for either three-tab or laminated shingles. AR products incorporating zinc and/or copper oxide modified admixtures with ceramic surface granules is widely practiced as an extension of current manufacturing technology. Evidence of water soluble ionic salt derivatives being the active microbiocides from these relatively inert source materials is commonly held by those skilled in the art, although the physical and chemical requirements to effect the conversion are typically misrepresented. Narayan et. al. (U.S. Pat. No. 5,356,664) describes incorporation of copper oxides in the ceramic protective coatings of granules as a source of this type microbiocide. Physically, formation of dew and absorption of sulfur and nitrogen oxides to yield a pH of 6.5–5.5 is prerequisite to acid displacement of the insoluble covalent bound copper in a heterogeneous interfacial surface reaction. Bond cleavage with concomitant loss of electrons in two steps yields divalent cupric cation in balance with acid anion as water soluble salt. Once released, diffusion away from the source in thermodynamic equilibration of concentration throughout the moisture film competes with the dynamics of drainage from the roof. The typical constricting pattern of inhibition trailing from metal components on residential roofs evidences an infinitesimal concentration gradient associated with dilution and drainage of soluble salt. This transient nature of the inhibitor combined with the site specific chemical requirements for its release belie general efficacy. And with regard to cupric oxide containing granules, inaccessibility within the ceramic protective coating and asphalt adherent create gross chemical inefficiencies. Exacerbating this situation, has been the industry's increased use of calcium carbonate filler in asphalt formulations which has reduced AR products' maintenance free life to approximately 1.5 years with lower end products. The trends in increased cleaning maintenance and use of dark color products are disturbing, particularly as in-roads to high end cement tile markets continue. Notwithstanding the numerous processing variants and trade secrets, the industry relies on a common AR technology which is inconsistent with performance claims. Given esthetics as the traditional driving force for product standards, the modification of ceramic coated granule processing for asphalt roof protection has lead to the present duplicity. Thus, this critical component of residential construction is becoming the highest maintenance and primary structural replacement item of the home.

OBJECTS OF THE INVENTION

It is an object of the present invention to provide composite roofing products with durable active microbiocide to resist fungus and algae growth under any environmental conditions.

It is a further object of this invention to provide an active microbiocide with sustained activity for the life of the roofing product despite surface erosion.

It is still a further object of this invention to incorporate active microbiocide in composite roofing products by adaptation to existing manufacturing processes.

It is another objective of this invention to replace dedusting oils for asphalt shingle ceramic granules with surface active microbiocides which are non-staining and enhance adhesion.

It is still another objective to circumvent release of metallic salts and organic microbes as well as cleaning maintenance requirements of composite roofing products.

These and other objects and advantages of the present invention will become more apparent to those skilled in the art when the instant disclosure is read in conjunction with the accompanying examples.

SUMMARY OF THE INVENTION

The above objects are achieved in the process of the present invention through matrix formulated active microbiocides which provide lasting surface protection. The fundamentals of specialty composite development have been widely practiced by chemical process industries, *Encyclopedia of Chemistry*, (Simon and Schuster, Macmillan) 1997, Vol. 2, pg. 387–389. Despite their compositional differences, both roofing products are amenable to the technology by token of organic sealant and asphalt saturant incorporated in composite tile and shingle, respectively. Stabilization of organic matrices to broaden applications via increased exterior life has been well developed through the use of specialty antioxidants and UV absorbers, Encyclopedia of Polymer Science & Engineering, (John Wiley & Sons, 2nd edition) 1985, Vol. 2. pg. 73–78. The mechanism of composite surface protection achieved with uniform matrix distribution of appropriate chemical inhibitors is well known to those skilled in the art. Molecular requirements for effective compatibility, non-volatility and chemical stability for this purpose are unique to both the substrate and targeted protection, *Polymer Reactions, Synthesis, Characterization, Reaction and Applications of Polymers*, 1989, *Pregmnon Press*, Vol. 6, Pg. 550–560. The above cited references are incorporated herein by reference.

Microbiocides of the present invention are organic complexes of divalent metal cations which are optimized by molecular design for specific composite matrices. The microbiocidal activity of divalent zinc, copper and tin is markedly increased in the form of lipophilic chelates and salts, which provide durable composite protection through matrix formulation. Specific matrix requirements as well as chemical and physical stability are achieved with commercial anionic surfactants. The divalent metallic complexes are readily prepared by aqueous exchange and the reaction mixtures per se can be effectively applied where water tolerances allow. Effective composite microbiocide concentration is related to both surface area and matrix formulation while lethal surface dosage is replenished by internal diffusion and exudation in response to any physical loss through weathering or maintenance. In this way, matrix formulation for durable effective inhibition of microbial growth is precisely analogous to that established for polymer processing and stabilization. A provision of organometallic microbiocide in matrix durable performance is established in topical thin film applications, Israel, U.S. Pat. No. 5,599,586.

In manufacture of extruded concrete tile, spray application of acrylate sealer is modified to limit penetration to internal voids via accelerated coalescence as Jordan disclosed in U.S. Pat. No. 4,571,415. For this purpose, the microbiocides are formulated with excess divalent cations to cross-link acrylate sealant to produce a polymer concrete surface. Sealant usage levels of 1 lb. per 100 sq. ft. can be controlled in matrix formation to a finite composite depth to provide lasting protection against both efflorescence and algae growth. Cast concrete roofing tile is similarly amenable to treatment. However, the very porous nature of these products argues for fundamental control of particle size distribution to reduce internal void volume and a post cure application to accommodate high temperatures.

A number of options exist in shingle processing for matrix formulation of microbiocides of the present invention. The direct addition to molten asphalt saturant typically filled with calcium carbonate, while affording uniform matrix distribution, would necessitate predrying the aqueous divalent metal complex. Alternatively, the aqueous reaction mixture would serve in pretreatment of filler feedstock during grinding to yield a surface coated filler with improved asphalt dispersability. With inherent surface activity, the organometallic chelates and salts would also serve in dedusting and asphalt adhesion of protective surfacing granules. As replacement for current auxiliary chemicals, integrated spray application of aqueous microbiocide to ceramic coated kiln product would permit process optimization and elimination of finished product stains. Incorporation of pretreated composite raw materials would release excess microbiocide throughout the molten asphalt during processing. Any one or combination of these options would afford uniform matrix distribution of active organometallic microbiocide by virtue of tailored molecular compatibility. Thus, through matrix formulation it is realistic to impart algae resistance for the duration of product life despite unavoidable erosion incurred in service. Equally, if not more, important is the potential for extended product life by avoiding damage incurred in maintenance cleaning.

DETAILED DESCRIPTION OF THE INVENTION

Matrix formulation of active microbiocides in composite concrete tile and asphalt shingle roofing products is essential for durable algae inhibition. The in depth body of polymer stabilization technology including criteria for molecular compatibility, stability and non-volatility is precisely applicable for microbiocides of the present invention. Composite protection via surface specific lethal concentration of matrix compatible microbiocides is both durable and controllable by internal diffusion and exudation in response to erosion losses. Divalent metal cations complexed with select anionic organic ligands in the form of microbiocidal salts and chelates uniquely meet all the chemical and physical properties for this purpose. Clearly, present commercial reliance on water soluble cationic salts released through weathering of passive sources suffers in this regard, particularly in shaded areas with relative high retained moisture and most prolific algae growth. In deference to site specific test decks, the observable growth patterns of both green and blue-green algae dictate evaluations encompassing widely ranging conditions as the basis of technical merit. Prolific growth on concrete tile or asphalt shingle often masks the cohabitation of green algae. The persistent dark colored protective sheath of blue-green algae in the presence of active microbiocides is reported by George, et.al. U.S. Pat. Nos. 5,415,919 and 5,316,824. Sodium hypochlorite readily decolorizes the staining residue and under supporting growth conditions evidences the early reappearance of green algae. The vitality of green algae permits qualitative performance evaluation of active micobiocides not previously practiced in this application. Tests involving re-colonization of sodium hypochlorite decolorized residential surfaces, confirm the relative toxicity of water soluble divalent salts of copper>zinc but more significant, the effectiveness of tin in meeting the objectives of the present invention. Most surprising and very unexpected is the magnitude of superiority of complexed tin and copper versus free ions of commercial systems; significantly advancing the state-of-the-art. A myriad of mono-, di- and poly- functional sulfates, sulfonates and carboxylates are available for sequestering and compatibilizing divalent cations for specific composite matrices. These microbiocides are readily prepared by mixing soluble inorganic divalent metal salts with appropriate organic anionic surfactants in aqueous media. Cationic exchange in binding dissociation equilibria shifts to the less soluble divalent organometallic complexes; ultimately to completion upon drying. These aqueous equilibrium reaction mixtures are used to advantage in processes which accommodate spray application and in-situ drying. Alternatively, the microbiocides can be spray dried with nucleating agents as required to produce free flowing powders. A generally applicable microbiocide composition would employ an anionic organic ligand sequestered 3 to 1 ratio of divalent copper to tin matrix formulated at 0.25% to 0.5% by weight.

While improved consolidation of concrete tiles has been achieved in extrusion processing, porosity and internal void volume remain as the source of effloresence and algae growth problems. Applied sealants only marginally reduce algae growth versus glaze coatings which are short lived relative to concrete tile. In the present invention, weatherable acrlyate sealant is formulated with active microbiocide providing a composite matrix with durable algae inhibition. Current extrusion lines, equipped for spray application of sealant and topical coatings, readily accommodate microbiocide incorporation. Options include reformulated acrylate sealant, in-line premixing and/or two stage addition. Sealing of uncured tile is made more effective by means of divalent metal cross linking to congeal the acrylate near the surface yielding a formulated matrix with interstitial contiguity. Alkyl polycarboxylate, alkaryloxyethoxy sulfate and/or alkyl esther sulfonate ligand sequestered 3 to 1 equivalent ratio of divalent copper to tin prepared with an excess of divalent metal cation satisfy all the matrix formulation requirements. Prepared as aqueous reaction mixtures, they can be incorporated directly as microbiocides and cross linking agents; stiochometry must be experimentally determined for each specific polymer and substrate. The resulting composite tile saturated with matrix formulated microbiocide to a depth of several centimeters would provide durable protection for the duration of product life. With approximately 7 years life, topical coatings are counter productive in this service where the future of high end roofing must rely on maintenance free performance.

In shingle manufacture, formulated molten asphalt used as binder for the base web and surfacing granules also serves as matrix for active microbiocide. The options for incorporation include molten asphalt formulation which necessitates separate stage drying of organometallic complexes. Alternatively, pre-treatment of composite raw materials permits utilization of the aqueous reaction mixtures with accompanying process efficiencies and improved product performance. Aryl-, alkiaryl- and/or alkyl-carboxylate, sulfate and sulfonate ligands satisfy both compatibility and thermal stability requirements; difunctionality is employed where substantivity offers advantage. Stiochometric equivalence of organic ligand with a 3 to 1 ratio of divalent copper to tin is preferred in composite shingles. The aqueous reaction mixture is suitable for direct application in treatment of calcium carbonate which is the predominate filler used to extend asphalt. Treatment of mill feed insures uniform surface coverage toward negating nutrient value and with incremental increase in operating temperature, in-situ drying. The benefits accruing through treatment of surfacing granules in kiln processing include increased asphalt adhesion and elimination of finished product stains; this by replacement of current water repellent and dedusting oil. The pretreatment of raw materials provides substantive surface coverage of composite particles and/or granules; the excess or multi-molecular layers are dispersed in the molten asphalt matrix. All components must be thoroughly dry prior to processing at approximately 400 degrees farenheight.

The inherent chemical stability and non-volatility of organometallic complex salts and chelates leaves compatibility as a system's specific requirement. Matrix formulation at 0.25% to 0.5% would provide algae protection during the life of the composite roofing product. In this regard, asphalt roofing systems are physically and chemically more fragile than tile. The gradual loss of surfacing granules, which provide the only protection of asphalt against UV catalyzed autoxidation, typically limits product life to 15 years in southern climates. It is significant and disconcerting for even topical maintenance treatments reported in U.S. Pat. No. 5,599,586 to survive product's terminal half life. With particular concern for the exposed shingle edge, incorporation of free radical scavengers and UV absorbers in matrix formulation could increase composite asphalt shingle life consistent with product claims.

The invention is further illustrated by the following examples in which durable surface protection is established through state-of-the-art matrix formulation technology and molecular microbiocide design for controlled performance.

EXAMPLE 1

Widely ranging commercial product variations and environmental conditions dictate broadly applicable test protocols as basis of algae inhibition. Residential surfaces exposed to sustained high moisture and indirect light evidence most aggressive growth patterns which in most cases represent cohabitation by blue-green and green algae. The more robust green algae recolonizes well in advance of blue-green algae following decolorizanion with sodium hypochlorite solution permitting evaluation of active microbiocide devoid of obscuring stains. Comparative evaluations were made of water soluble divalent metal salts representing commercial systems and the complexed reaction mixtures of the present invention resulting from their exchange with stiochometric equivalents of monovalent cations of organic ligands. Horizontal surfaces were used in all cases to nanimize dilution and/or drainage of chemicals which were spray applied at 0.25% in aqueous media. Treated surfaces were examined 3 times daily and tests were terminated in the event of rain or after 3 days/dew cycles. Parallel tests were run on concrete and coated surfaces with confirming replications. The results tabulated below clearly indicate the relative toxicity of divalent Zn<Cu<Sn, and most significantly an order of magnitude greater effectiveness of complexed tin, in addition to the lethal threshold concentrations for matrix formulation. It is precisely this surface protection that can be sustained during composite product life through matrix formulation of compatibilized divalent metallic chelates and salts of the present invention. The aqueous reaction mixtures offer broad flexibility in both composition and application with exchange equilibria ultimately yielding divalent metal chelates and salts upon drying. Excess soluble divalent metal ions effectively cross link anionic polymers while stiochometric equivalence with difunctional ligands produces chelate oligomers. In addition to surface durability via matrix compatibility, these active microbiocides exhibit no measurable vapor pressure and exceptional chemical stability. The combination of cupric and stannous complexes for inhibition of both green and blue-green algae is clearly a preferred embodiment. The mono- and di-functional ligands used in these test were sodium salts of dioctylsulfosuccinate/Emcol 4500 from Witco Chemical and dihexadecyldiphenyl oxide disulfonate/Dowfax 8390 from Dow Chemical. They are but examples from among the numerous commercial offerings of anionic sulfonates, sulfates and/or carboxylates useful for matrix compatibilization and optimization of divalent metal microbiocides. The ultimate selections must be empirical and based on laboratory evaluation of specific matrix formulations.

| Microbiocide composition | Stiochometry | Weight % divalent cation | Observed mortality | Comments |
|---|---|---|---|---|
| Ionic salt solutions | | | | |
| Zn++acetate | | 36 | >72 hr.. | unchanged |
| Cu++sulfate | | 40 | 72 hr.. | 50% complete |
| Sn++chloride | | 63 | 24 hr.. | complete |
| Complexed ions | | | | |
| Cu++: sulfonate | 1:2 | 6 | 36 hr.. | 90% complete |
| Cu++: disulfonate | 1:1 | 8 | 36 hr.. | complete |
| Sn++: sulfonate | 1:2 | 12 | <4 hr.. | complete |
| Sn++: disulfonate | 1:1 | 14 | <4 hr.. | complete |
| Cu++/Sn++(3/1): disulfonate | 1:1 | 10 | <4 hr.. | complete |

EXAMPLE 2

Moisture intrusion in composite concrete is a common problem throughout industry. Current technology to control residual porosity of roof tile centers on particle size distributions to minimize internal void volume and polymer sealants as a barrier against moisture penetration. Despite advances achieved in extrusion processing, the technology has not been fully exploited with regard to copolymer acrylic sealants. The application of 50% aqueous sealant to uncured tile extrudate evidences its facile penetration to internal pores with substantial surface area; this in the absence of requisite surface saturation and interstitial contiguity. At line speeds in the range of 150 ft./min. and sealant application of 1 lb./100 sq. ft. the process is amenable to accelerated coalescence to congeal polymer at the tile face. Divalent metal cross-linking with a nominal excess of free divalent cations is an inherent provision of organometallic microbiocides for the purpose. Notably, few crosslinks exhibit a substantial modification in rate of polyacrylate coalescence because of their exceptionally high average molecular weight. An incremental viscosity increase toward that of glaze coatings would also reduce sealant penetration. The rate of polymer coalescence and organometallic complex compatibility are laboratory determined for specific sealant and substrate. Film clarity of formulated matrix at 0.5% by weight microbiocide in the absence of surface blooming is qualifyng. Ethoxylated alcohol half ester of disulfosuccinate/Emcol 4300 from Witco ChemicaL polycarboxylate/Tamol 850 from Rohm & Haas and nonylphenoxypolyetheroxy sulfate/Triton XN-45S from Union Carbide are preferred anionic ligands based on functionality and compatibility in copolymer acrylics. As formulated sealants, elastomeric and thermoplastic acrylic copolymers have proven weatherability and physical properties for durable composite polymer concrete. The microbiocide polymer matrix, formulated to advance coalescence provides effective sealant control and microbiocide performance.

EXAMPLE 3

The filled asphalt matrix of composite roofing shingles incorporating 0.5% divalent metal complexes would provide product life protection against algae discoloration. Alkyl-, aryl- and alkaryl-calboxylate, sulfate and sulfonate ligands readily compatibilize divalent metal cations in the asphalt hydrocarbon mixures; inherent non-volatility and chemical stability being instrumental for high temperature processing. Formulation in molten asphalt requires that the active metal chelates and salts be devoid of moisture; thus the aqueous reaction mixture is spray or disc dried with nucleating agent as needed for product handling properties. Readily available dodecylbenzene-, C 14–16 olefin- and polynaththalene-sulfonate sodium salts exchanged with stiochometric equivalent of 3 to 1 ratio copper to tin is preferred. Improved matrix formulation rheology and absence of surface film/blooming are ultimate determining factors.

Alternatively, with integrated raw material sourcing or custom production, manufacturers' have the option of pretreating asphalt fillers. Using ligands similar to those described above, spray application of the aqueous cupric-stannous reaction mixture during grinding to approximately minus 200 mesh yields uniform surface coverage of newly formed particle surfaces and insitu drying with increased flue gas temperature in typical classifying mills. The surface activity of these microbicide coatings improves dispersability of filler particles via hydrophobic wetting. At 0.5% by weight of the matrix formulation, the applied coating will equilibrate providing a uniform concentration through out the asphalt and a retained monomolecular surface coating. The potential synergy in negating the nutrient value of calcium carbonate leverages this approach.

Because composite granules are only partially embedded, the microbiocide mixture can be tailored to both mineral surface substantivity and asphalt compatibility. Monofunctional organic ligands yield divalent metal chelates and salts providing optimum adhesion to asphalt and effective in process granule dedusting. Equally important, is the elimination of finished products stains encountered with hydrocarbon oil dedusting. Partial incorporation of difunctional organic ligands would increase surface substantivity and durability via chelate oligmer formation; sodium salts of dihexadecyl diphenyl oxide disulfonatetDowfax 8390 and ethoxylated alcohol half ester sulfosuccinate/Emcol 4300 are exemplary. The release of microbiocide to molten asphalt during embedment with retained granule surface coating to promote adhesion offers durable algae resistance as well as needed process improvements. Considering the relatively low granule surface area, spray application of 0.3% coating using the aqueous reaction mixture at an effective concentration for uniform distribution and evaporative cooling of kiln furnace product would satisfy composite requirements.

I claim:

1. A method of protecting a composite roofing product against algae discoloration, comprising;

(a) forming a roofing product comprising (b) a weatherable organic matrix and (c) compatible divalent metal chelates and/or salts wherein the weatherable organic matrix is employed as binder and/or sealer of the composite roofing product and contains 0.1 to 4.0 weight percent of the compatible divalent metal chelates and/or salts.

2. The method of claim 1 in which the composite roofing product is concrete tile containing a sealer manufactured in the steps comprising concrete extrusion, application of an organic sealer and product curing wherein the sealer contains divalent metal chelates and/or salts, and forms an organic sealer matrix within the extruded concrete.

3. The method of claim 2 wherein the sealer comprises (a) an elastomeric and/or thermoplastic acrylic copolymer and (b) divalent zinc, tin and/or copper complexes of organic sulfates, sulfonates and/or carboxylates.

4. The method of claim 3 wherein the acrylic copolymer sealer containing the divalent metal chelates and/or salts is applied to at least the surface of the concrete tile.

5. The method of claim 4 wherein the sealer comprises 96 to 99.9 weight percent acrylic copolymer and 0.1 to 4.0 weight percent divalent metal chelates and/or salts.

6. The method of claim 5 wherein the divalent metal chelates and/or salts maintain an equivalent weight ratio of divalent metal to organic sulfate, sulfonate and or carbxylate in the range of 0.5 to 1.5.

7. The method of claim 6 wherein the divalent metal chelates and/or salts maintain a 1:1 to 2:1 equivalent weight ratio of divalent copper to tin complexed with alkyl polycarboxylates, alkaryloxyethoxy sulfates and/or alkyl ester sulfonates.

8. The method of claim 1 in which the composite roofing product is asphalt shingle manufactured in steps comprising coating a base web with molten asphalt formulation, adhering surfacing granules to the coated base web and coding wherein the molten asphalt formulation comprising filler and divalent metal salts and/or chelates forms the organic binder matrix within the composite asphalt shingle.

9. The method of claim 8 wherein the organic binder matrix comprises (a) a calcium carbonate filled asphalt formulation and (b) divalent zinc, tin and/or copper complexes of organic sulfates, sulfonates and/or carboxylates.

10. The method of claim 9 wherein the divalent metal chelates and/or salts are combined with the calcium carbonate or surfacing granules prior to their distribution into the molten asphalt formulation.

11. The method of claim 10 wherein the divalent metal chelates and/or salts are combined by spraying on to (a) the calcium carbonate filler and/or (b) the ceramic surfacing granules wherein the combination of divalent metal chelates and/or salts and inorganic components are used in formation of the organic asphalt binder matrix of the composite.

12. The method of claim 11 wherein the asphalt matrix binder formulation comprises 96 to 99.9 weight percent filled asphalt and 0.1 to 4.0 weigh percent divalent metal chelates and/or salts.

13. The method of claim 12 wherein the divalent metal chelates and/or salts maintain equivalent weight ratio of divalent metal to organic sulfate, sulfonate and/or carbxylate in the range of 0.6 to 1.4.

14. The method of claim 13 wherein the divalent metal chelates and/or salts maintain a 1:1 to 2:1 equivalent weight ratio of divalent copper to in complexed with alkyl, alkaryl and/or aryl sulfates, sulfonates and/or carboxylates.

15. The method of claim 8 wherein the divalent metal chelates and salts are incorporated directly into the molten asphalt binder matrix.

* * * * *